US010448919B2

United States Patent
Leal et al.

(10) Patent No.: US 10,448,919 B2
(45) Date of Patent: Oct. 22, 2019

(54) ASSESSING JOINT CONDITION USING ACOUSTIC SENSORS

(71) Applicant: Kneevoice, Inc., Los Angeles, CA (US)

(72) Inventors: Carlos Leal, Bogota (CO); Felipe Rigby, Bogota (CO); Gustavo De Greiff, Santa Monica, CA (US)

(73) Assignee: KNEEVOICE, INC., Los Angeles, CA (US)

( * ) Notice: Subject to any disclaimer, the term of this patent is extended or adjusted under 35 U.S.C. 154(b) by 21 days.

(21) Appl. No.: 15/887,638

(22) Filed: Feb. 2, 2018

(65) Prior Publication Data

US 2018/0153501 A1  Jun. 7, 2018

Related U.S. Application Data

(63) Continuation of application No. PCT/US2016/065380, filed on Dec. 7, 2016.

(60) Provisional application No. 62/264,603, filed on Dec. 8, 2015.

(51) Int. Cl.
| | |
|---|---|
| A61B 7/00 | (2006.01) |
| A61B 5/107 | (2006.01) |
| A61B 5/00 | (2006.01) |
| A61B 8/08 | (2006.01) |
| G16H 50/30 | (2018.01) |
| G16H 20/30 | (2018.01) |

(52) U.S. Cl.
CPC .............. *A61B 7/006* (2013.01); *A61B 5/107* (2013.01); *A61B 5/4514* (2013.01); *A61B 5/4528* (2013.01); *A61B 7/00* (2013.01); *A61B 8/0875* (2013.01); *G16H 20/30* (2018.01); *G16H 50/30* (2018.01)

(58) Field of Classification Search
CPC ......... A61B 7/006; A61B 5/4514; A61B 7/00; A61B 8/00; A61B 8/08; A61B 8/0858; A61B 8/00875; A61B 5/00
See application file for complete search history.

(56) References Cited

U.S. PATENT DOCUMENTS

| | | |
|---|---|---|
| 8,372,153 B2 | 2/2013 | Roche |
| 2003/0065264 A1 | 4/2003 | Tsoref et al. |
| 2004/0054302 A1* | 3/2004 | Czernicki .............. A61B 7/006 600/586 |

(Continued)

OTHER PUBLICATIONS

Kim et al. 'An Acoustical Evaluation of Knee Sound for Noninvasive Screening and Early Detection of Articular Pathology'; Jun. 17, 2010; J Med Syst (2012) 36:715-722.*

(Continued)

*Primary Examiner* — Patrick Fernandes
(74) *Attorney, Agent, or Firm* — Foley Hoag LLP; David P. Halstead; Erik Huestis

(57) ABSTRACT

A new non-invasive tool for cartilage assessment, exercise and sports management, and prevention of osteoarthritis is provided. In various embodiments, cartilage condition is assessed using audible signals from joints. Assessment test results are used to provide feedback regarding joint stress and friction that is related to physiological or pathological loads. Data obtained from audible signals are processed to provide an index that can be interpreted by a user or third parties. The index is useful as a baseline for exercise practices, training routines, wellness programs, or rehabilitation protocols.

24 Claims, 13 Drawing Sheets

(56) References Cited

U.S. PATENT DOCUMENTS

| | | | | |
|---|---|---|---|---|
| 2005/0015002 A1* | 1/2005 | Dixon | ............... | A61B 5/1038 |
| | | | | 600/407 |
| 2005/0240446 A1* | 10/2005 | Berry | ................ | G06F 19/325 |
| | | | | 705/3 |
| 2006/0062448 A1* | 3/2006 | Hirsch | ............... | A61B 5/0059 |
| | | | | 382/154 |
| 2007/0106127 A1* | 5/2007 | Alman | ............... | A61B 5/0002 |
| | | | | 600/300 |
| 2008/0013747 A1* | 1/2008 | Tran | ............... | A61B 7/04 |
| | | | | 381/67 |
| 2009/0281981 A1* | 11/2009 | Chen | ............... | G06K 9/6282 |
| | | | | 706/56 |
| 2014/0056432 A1* | 2/2014 | Loui | ............... | G10L 25/51 |
| | | | | 381/56 |
| 2014/0221825 A1 | 8/2014 | Mahfouz et al. | | |

OTHER PUBLICATIONS

International Search Report and Written Opinion for International Application No. PCT/US2016/065380, dated Apr. 6, 2017.

\* cited by examiner

ASSESSING JOINT CONDITION USING ACOUSTIC SENSORS

CROSS-REFERENCE TO RELATED APPLICATIONS

This application is a continuation of International Application No. PCT/US16/65380, filed Dec. 7, 2016, which claims the benefit of Provisional Application No. 62/264,603, filed Dec. 8, 2015, which applications are hereby incorporated by reference in their entireties.

TECHNICAL FIELD

The systems and methods described herein relate to assessing joint condition using acoustic sensors.

BACKGROUND

The main function of cartilage is to provide joint motion with low friction. Joint damage is known as chondromalacia or osteoarthritis, a painful and limiting condition that comes with aging in a natural form, or in an early onset due to overload or articular deformities. Once the cartilage is damaged, it is usually replaced by a fibrous tissue that resembles the hyaline network, which never has the same biomechanical properties of the original cartilage. Worse, the main symptom of joint damage, pain, usually appears only when there are already irreversible injuries. Diagnosis of osteoarthritis or patellofemoral chondromalacia is therefore simple in advanced states, but uncertain and variable in early stages. In a medical environment, it is difficult to determine prognosis or to assess benefits of interventions with conventional diagnostic and imaging tools. The use of diagnostic images is expensive and exposes a patient to an irradiation risk. Arthroscopic or invasive diagnostic procedures may have side effects and complications. Moreover, it is difficult to assess cartilage condition during physical activities, in order to safely partake in exercise and sports. Thus there exists a need in the art for systems and methods for evaluating and predicting cartilage joint condition, including health and well-being.

BRIEF SUMMARY

It is a realization of the inventors that isolated joint noise emissions provide an opportunity to study and identify patterns of friction, crepitus, or joint cracks in a simple and non-invasive way. Previous efforts to develop phonoarthrography systems were not only technologically limited, but were directed toward the femoro-tibial joint. Such systems were plagued by a large number of acoustic sources that drowned out signals of interest. By focusing instead on a joint associated with sounds that may be isolated (e.g., the patellofemoral joint, to name an illustrative example), the inventors have developed a system to quantify joint condition, which may be used in diagnosing injury, evaluating health or well-being, studying the effects of therapeutic interventions, or other suitable tasks. In exemplary embodiments, patellofemoral joint acoustic emissions are quantified using high definition acquisition systems. A measurable and comparable score is generated, and provide a solid recommendation of exercise and wellness of the joint, and therefore of the physical activity of the user or patient. By providing ongoing feedback to a user, for example in the form of a joint health score, systems and methods according to the present disclosure enable the user to realize increased performance, foster a healthy lifestyle, reduce the risk of injury, and avoid costly interventions such as surgery or joint replacement.

In certain aspects, the system described herein assesses cartilage condition. In such aspects, the system comprises at least one acoustic sensor, a user database configured to store data associated with a first user, and a processor operatively connected to the user database. The processor is configured to receive a signal from the at least one acoustic sensor, identify at least one first sound parameter associated with the signal, identify at least one second sound parameter associated with the first user from the user database, and identify a condition of cartilage based on a comparison of the at least one first sound parameter with the at least one second sound parameter. In some implementations, the data associated with the first user may comprise one or more of age data, gender data, a body mass index, activity data, medical history data, historic acoustic signals associated with the cartilage of the first user, knee symptom data, or other suitable data. The second sound parameter may be a function of the data associated with the first user or may be based on data of a set of users similar to the first user.

In some implementations, the signal from the at least one acoustic sensor is associated with a patellofemoral joint of the first user.

In some implementations, the at least one acoustic sensor is configured to cover an anterior patellar region.

In some implementations, the at least one acoustic sensor comprises a concave surface. In some such implementations, at least 90% of the surface area of the concave surface contacts an anterior patellar region of the first user.

In some implementations, the at least one acoustic sensor comprises a resilient surface.

In some implementations, the at least one acoustic sensor comprises a contact microphone.

In some implementations, the system further comprises an adhesive that releasably couples the at least one acoustic sensor to a patella of the first user. In some such implementations, the adhesive comprises an acoustic gel.

In some implementations, the processor is further configured to denoise the signal, which may include one or more of: averaging data taken during two, three, four, five, or more cycles of an active flexo-extension motion by the first user; comparing the signal with one or more predetermined noise patterns; comparing the signal with a supplemental signal received from at least one supplemental acoustic sensor; or other suitable denoising techniques.

In some implementations, the processor is further configured to transmit a message to the first user, which may include instructions for completing a cartilage condition assessment. In implementations in which the processor instructs the first user how to complete a cartilage condition assessment, the processor may be further configured to determine whether the first user has completed a first cartilage condition assessment within a predetermined period of time, and, if not, to prompt the first user to complete a cartilage condition assessment. The predetermined period of time may be one month, three weeks, two weeks, one week, or some other suitable period of time. In some implementations, the processor is further configured to administer a second cartilage condition assessment to the first user within a period of time after user exercise, a possible injury, or a medical intervention. As an illustrative example of such an implementation, the processor may receive a message from a second user (such as a coach or guardian of the first user) indicating when a practice session has been completed, and may respond to the message by prompting the first user to complete a cartilage condition assessment.

In some implementations, the processor is further configured to output an indicator representative of the cartilage condition assessment to a second user, who may be a coach, a legal guardian, a referee, an umpire, a trainer, a medical professional, a physical therapist, a friend, a family member, a member of a peer group, a teammate, a member of a social media group, or some other suitable second party.

In some implementations, the processor is further configured to receive second sensor data associated with the first user, wherein the cartilage condition assessment is determined based on the second sensor data. Such data may include accelerometer data, touchscreen data, or other suitable data. In such implementations, the processor may be further configured to correlate the second sensor data with the signal from the at least one acoustic sensor. In such implementations, the processor may be further configured to identify a knee angle, a knee angular velocity, or other suitable information.

In some implementations, the at least one acoustic sensor comprises a wireless transmitter.

In some implementations, the processor is further configured to suggest an exercise regime based on the condition of the cartilage.

In some implementations, the processor is further configured to identify when a patella enters and leaves the trochlear groove during flexion.

In some implementations, the processor is further configured to identify a location of and/or contact a medical care facility near the first user.

In certain aspects, the computer-implemented method described herein assesses cartilage condition. In such aspects, the method comprises receiving a signal from at least one acoustic sensor, identifying at least one first sound parameter associated with the signal, identifying at least one second sound parameter based on data associated with the first user, and identifying a condition of cartilage based on a comparison of the at least one first sound parameter with the at least one second sound parameter. In some implementations, the data associated with the first user may comprise one or more of age data, gender data, a body mass index, activity data, medical history data, historic acoustic signals associated with the cartilage of the first user, knee symptom data, or other suitable data. The second sound parameter may be a function of the data associated with the first user or may be based on data of a set of users similar to the first user.

In some implementations, the signal from the at least one acoustic sensor is associated with a patellofemoral joint of the first user.

In some implementations, the at least one acoustic sensor is configured to cover an anterior patellar region.

In some implementations, the at least one acoustic sensor comprises a concave surface. In some such implementations, at least 90% of the surface area of the concave surface contacts an anterior patellar region of the first user.

In some implementations, the at least one acoustic sensor comprises a resilient surface.

In some implementations, the at least one acoustic sensor comprises a contact microphone.

In some implementations, the method further comprises releasably coupling the at least one acoustic sensor to a patella of the first user.

In some such implementations, the method further comprises contacting a joint and the at least one acoustic sensor with an acoustic gel.

In some implementations, the method further comprises denoising the signal, which may include one or more of: averaging data taken during two, three, four, five, or more cycles of an active flexo-extension motion by the first user; comparing the signal with one or more predetermined noise patterns; comparing the signal with a supplemental signal received from at least one supplemental acoustic sensor; or other suitable denoising techniques.

In some implementations, the method further comprises transmitting a message to the first user, which may include instructions for completing a cartilage condition assessment. In implementations in which the message includes cartilage condition assessment instructions, the method may further comprise determining whether the first user has completed a first cartilage condition assessment within a predetermined period of time, and, if not, prompting the first user to complete a cartilage condition assessment. The predetermined period of time may be one month, three weeks, two weeks, one week, or some other suitable period of time. In some implementations, the method further comprises administering a second cartilage condition assessment to the first user within a period of time after user exercise, a possible injury, or a medical intervention. As an illustrative example of such an implementation, the method may prompt the first user to complete a cartilage condition assessment once a second user (such as a coach or guardian of the first user) has indicated that a practice session has been completed.

In some implementations, the method further comprises outputting an indicator representative of the cartilage condition to a second user, who may be a coach, a legal guardian, a referee, an umpire, a trainer, a medical professional, a physical therapist, a friend, a family member, a member of a peer group, a teammate, a member of a social media group, or some other suitable second party.

In some implementations, the method further comprises receiving second sensor data associated with the first user, wherein the cartilage condition is based on the second sensor data. Such data may include accelerometer data, touchscreen data, or other suitable data. In such implementations, the method may further comprise correlating the second sensor data with the signal from the at least one acoustic sensor. In such implementations, the method may further comprise identifying a knee angle, a knee angular velocity, or other suitable information.

In some implementations, the at least one acoustic sensor comprises a wireless transmitter.

In some implementations, the method further comprises suggesting an exercise regime based on the condition of the cartilage.

In some implementations, the method further comprises identifying when a patella enters and leaves the trochlear groove during flexion.

In some implementations, the method further comprises identifying a location of and/or contact a medical care facility near the first user.

In certain aspects, a method of and computer program product for joint assessment is provided. In such aspects, audio is received comprising sounds emanating from a human joint. A plurality of features is extracted from the audio. The plurality of features is provided to a trained classifier. A first score indicative of joint health is obtained from the trained classifier. In some implementations, the audio is captured via a contact microphone substantially in contact with a human.

In some implementations, noise is canceled from the audio prior to extracting the plurality of features. In some such implementations, an ambient audio signal is captured and the ambient audio signal is removes from the audio. In some such implementations, a bandpass filter is applied to the audio.

In some implementations, the features comprise signal frequency, amplitude, zero-crossing rate, entropy of energy, spectral centroid, spectral spread, mel-frequency cepstral coefficients, or chroma vector.

In some implementations, the trained classifier comprises a random decision forest. In some implementations, the trained classifier comprises a neural network. In some implementations, the trained classifier comprises a support vector machine.

In some implementations, a second score indicative of joint health is computed from the first score. In some such implementations, computing the second score comprises weighting the first score according to a reported pain value. In some such implementations, computing the second score comprises weighting the first score according to a reported pain value. In some such implementations, computing the second score comprises weighting the first score according to a characteristic of a subject. In some implementations, the characteristic comprises body mass index, age, gender, existing medical condition, or frequency of physical activity.

BRIEF DESCRIPTION OF THE DRAWINGS

The systems and methods described herein are set forth in the appended list of claims. However, for the purpose of explanation, several implementations are set forth in the following drawings.

DETAILED DESCRIPTION

In the following description, numerous details are set forth for the purpose of explanation. However, one of ordinary skill in the art will realize that the implementations described herein may be practiced without the use of these specific details and that the implementations described herein may be modified, supplemented, or otherwise altered without departing from the scope of the systems and methods described herein.

The systems and methods described herein relate to assessing cartilage condition, including health and well-being. Noises made by a joint during motion are related to the condition of the joint. As such, analyzing such noises in light of other user information (e.g., age, gender, medical history, or other suitable data) allows earlier detection of cartilage problems. A user's joint noises are recorded, denoised, and compared to noises made by similar users to generate a joint health score and recommendations for user action. In some implementations, recommendations are generated and provided to a user based on data collected from similar users. By providing ongoing feedback to a user, for example in the form of a joint health score, systems and methods according to the present disclosure enable the user to realize increased performance, reduce the risk of injury, foster a healthy lifestyle, and avoid costly interventions such as surgery or joint replacement.

Figure 1:
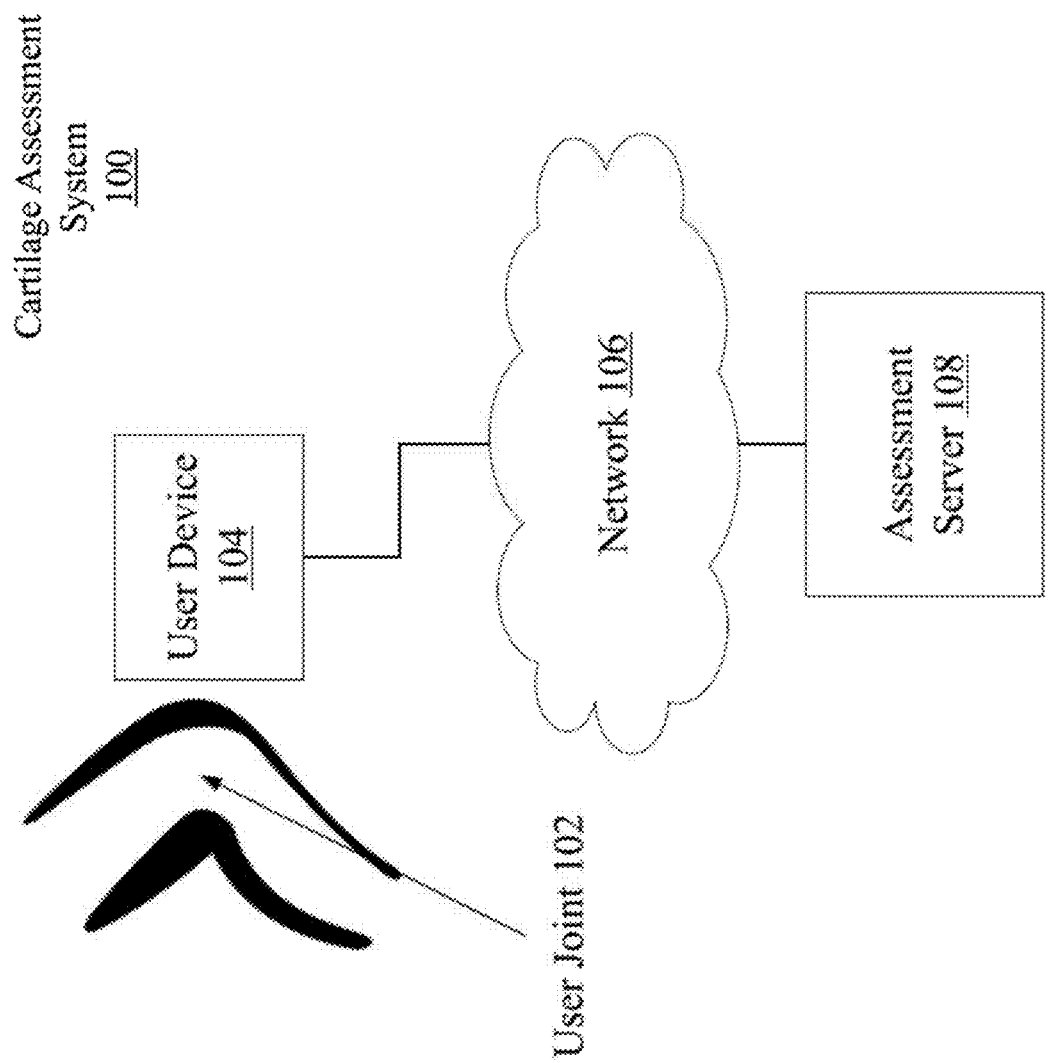
FIG. 1 is a block diagram of a cartilage assessment system, according to various embodiments of the present disclosure.

FIG. 1 is an illustrative block diagram of a cartilage assessment system 100, which assesses the condition of a user's joint, here depicted as a knee. As depicted, sounds from a user joint 102 are measured and recorded by user device 104, which is described in more detail in relation to FIG. 2. User device 104 may continuously or periodically monitor acoustic signals from a joint, or may administer joint condition assessment to a user (e.g., by requesting the user perform certain actions while the device collects acoustic signals) and provide results to the user being evaluated. In some implementations, results are provided live to a user. In other implementations, results are provided asynchronously, for example at a predetermined time, upon results reaching a certain threshold, or upon request by a user. In some implementations, user device 104 may also provide results to other users associated with the user being evaluated, such as coaches, legal guardians, referees, umpires, trainers, medical professionals, physical therapists, friends, family members, members of a peer group, teammates, members of a social media group, or other suitable users. There may be a different number of user devices 104 than are depicted here, and there may be a different number of users being evaluated and/or users receiving evaluation results. Information regarding user assessments and evaluations may be transmitted to and from a user device 104 through network 106. Network 106 is a computer network, and in certain implementations may be the Internet. Assessment server 108 may store user information, analyze user data, or both, and may be a server, a personal computer, a mainframe, a cluster of computing devices, or some other suitable computing device. Assessment server 108 is described in more detail in relation to FIG. 3. In some implementations, one or more user devices 104 may store all relevant data and perform all relevant analysis, and there is no assessment server 108. In some embodiments, assessment server 108 is resident in a mobile device such as a smartphone. In such embodiments, network 106 may include a Bluetooth connection, a wireless network such as provided under IEEE 802.11, or any of various ad hoc wireless networks known in the art.

Figure 2:
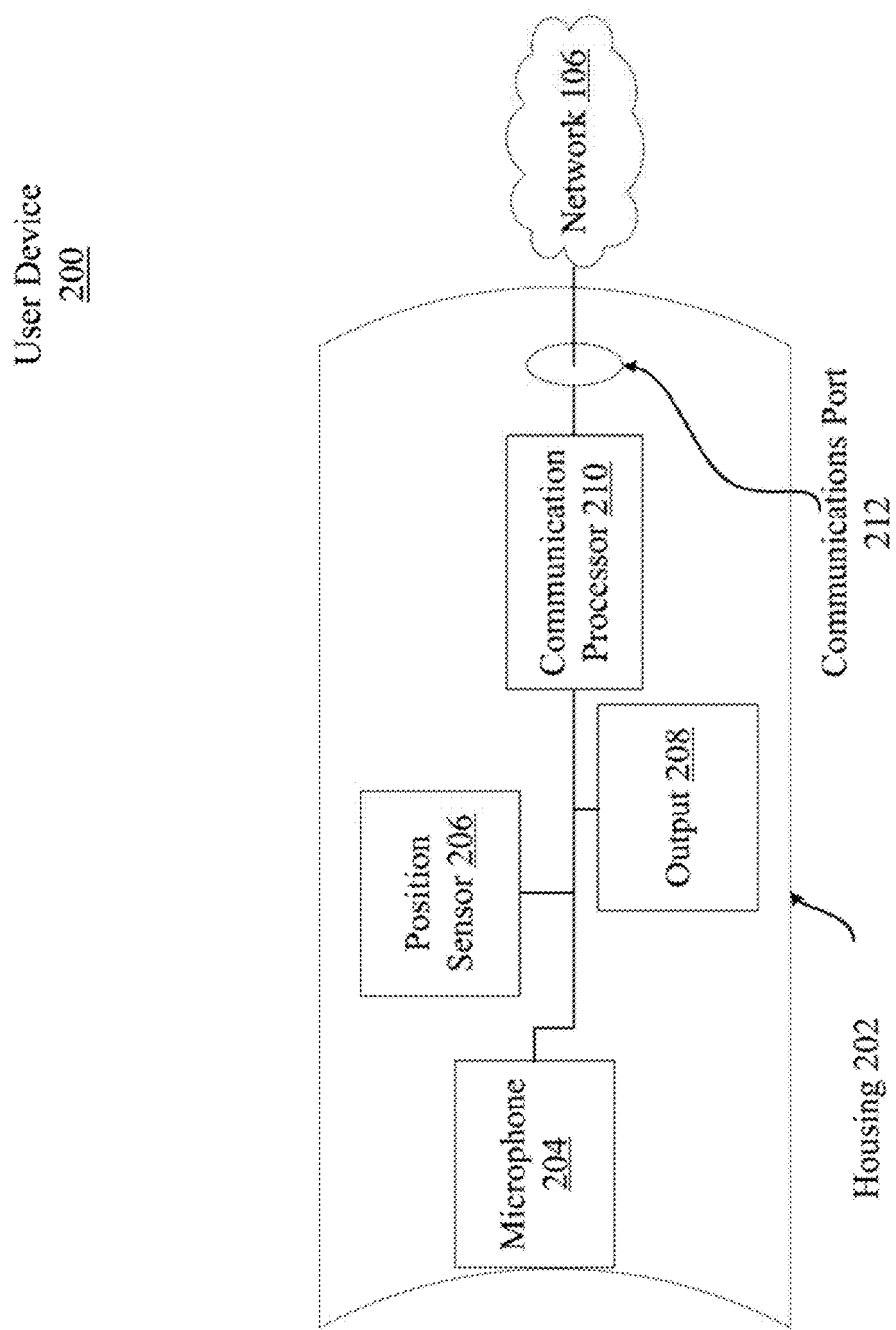
FIG. 2 is a block diagram of a user device, according to various embodiments of the present disclosure.

FIG. 2 is an illustrative block diagram of a user device 200, which may be a wireless microphone, a smartphone, a tablet computer, a personal laptop computer, a wearable computing device, or some other suitable device. User device 200 may act as the user device 104 of FIG. 1. User device 200 records sounds emitted from joints, e.g., continuously, periodically, at varying intervals, or in response to certain motions or other signals, and in some implementations may further provide instructions to a user for performing certain actions, record cartilage sounds, display joint evaluations to a user, transmit evaluations to an authorized user, suggest follow-up steps to a user, or perform other suitable tasks. User device 200 may be in contact with a user joint being evaluated with housing 202, and may record noises with microphone 204. Position sensor 206 may record data relating to the one or more of the orientation and position of user device 200 or of user joint 102. Output 208 may output instructions for performing a joint condition assessment, results of a joint condition assessment or evaluation, or other suitable information. Communications processor 210 may send and receive information regarding joint evaluations and assessments through communication port 212. In some embodiments, assessment server 108 is resident in user device 200. In some such embodiments, network 106 is omitted.

As depicted, housing 202 is adapted to contact the anterior portion of a knee or some other suitable joint, but housing 202 may have a different form than is here depicted. In some implementations, housing 202 is resilient in whole or in part, which may allow housing 202 to conform to the shape of a joint. In some implementations, housing 202 may further include a fastener for removably securing housing 202 to a joint, such as a resilient band or some other suitable implement. In some embodiments, housing 202 is adapted to insulate microphone 204 from external sounds, and thus increase the quality of recording. Various microphone insulation techniques and materials are known in the art, including foam, baffles, and shock absorption structures.

Microphone 204 may include one or more acoustic sensors, such as a contact microphone, a ribbon microphone, or other suitable acoustic sensor. Microphone 204 may be a unidirectional microphone, and may be positioned in housing 202 such that, when in use, it records noises from joint 102 and not from other directions. Sound data generated by microphone 204 may be transmitted to assessment server 108 by communication processor 210 for processing. In some implementations, user device 200 includes separate, additional microphones positioned to pick up additional sounds created by other joints, and assessment server 108 may compare signals from the additional microphones to the signal from microphone 204 to isolate sound generated by a joint of interest from noise generated by other joints. As an illustrative example of such an implementation, microphone 204 may be positioned to record sound generated by a patellofemoral joint, while additional microphones may be positioned to record noise generated by a femorotibial joint, and assessment server 108 may account for the noise generated by the femorotibial joint in analyzing sound recorded by microphone 204. In some implementations, microphone 204 may be remote from user device 200, and may transmit information to user device 200 through a USB connection, a BLUETOOTH connection, or some other suitable connection.

Position sensor 206 may be an accelerometer, a potentiometer, an incline sensor, a compass, a gravimeter, a strain gauge, piezoelectric sensor, or some other device suitable for generating data indicating one or more of a position and an orientation of user device 200. Assessment server 108 may compare data from position sensor 206 to data from microphone 204 to correlations between sounds made by the joint and the joint's position and angular velocity; assessment server 108 may further base joint condition assessments on such correlations. In some implementations, user device 200 may include a different number of position sensors 206 than are here depicted, including zero such position sensors.

Output 208 may be a LCD screen, a speaker, an LED array, a touchscreen, or some other device suitable for providing information to a user. Output 208 may output instructions or assessments received from assessment server 108 via communication processor 210. In some implementations, user device 200 may include a different number of outputs 208 than are here depicted, including zero such outputs.

Communication processor 210 may be a computer processor that sends and receives information via communications port 204. Communication processor 210 may receive joint condition assessment instructions or other suitable information, and may transmit sound data, position data, device identification data, or other suitable data.

The depicted communication port 212 is a network port which transmits data via network 106. The data transmitted may include sound data, position data, or other suitable information. Communication port 212 may include a 100BASE-TX port, a 1000BASE-T port, a 10 GBASE-T port, a WI-FI antenna, a BLUETOOTH antenna, a cellular antenna, or any other suitable network port. In certain implementations, there may be a different number of ports than are depicted. In certain implementations, communication port 212 may provide secure communications, such as by using the Secure Sockets Layer (SSL) protocol, the Transport Layer Security (TLS) protocol, or other suitable protocol.

User device 200 is configured to contact a joint and record the sounds it generates. Housing 202 may be configured to conform to the joint, and microphone 204 may record sounds from the joint. Position sensor 206 may record data indicating the position, velocity, or other suitable data related to joint condition that may be correlated with the sounds recorded by microphone 204. Output 208 may instruct a user regarding how to use user device 200 and present results of a cartilage condition assessment. Communication processor 210 may transmit such data to a device for processing via communications port 212 and network 106. In some implementations, user device 200 may incorporate additional elements, such as a user input device that may allow a user to indicate which joint the user device 200 will be recording and when an assessment has begun or been completed; a data processor that preprocesses or analyzes data; or other suitable elements. In some implementations, user device 200 may include a different number of elements than are here depicted; as illustrative examples, a user device 200 may exclude a position sensor 206, or include additional microphones 204.

Although it is depicted as a single unit, user device 200 may be implemented over more than one device. As an illustrative example, housing 202 may secure a microphone, a position sensor, and a BLUETOOTH communication device to a joint; in such an implementation, information from the sensors in housing 202 may be transmitted locally to another user device (e.g., a cellular phone, a laptop computer, or some other suitable device), which may in turn communicate with assessment server 108 over network 106.

Figure 3:
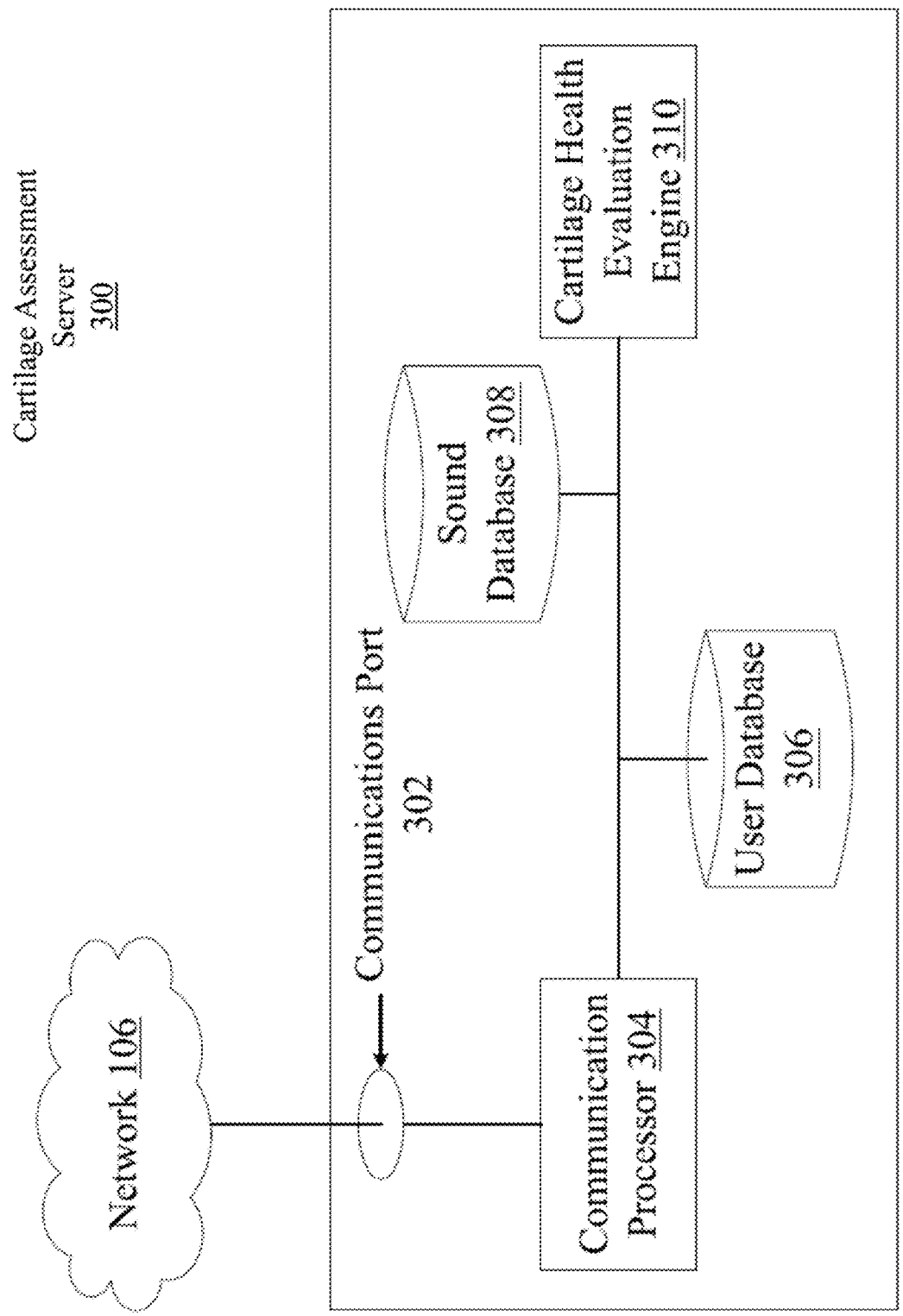
FIG. 3 is a block diagram of a cartilage evaluation server, according to various embodiments of the present disclosure.

FIG. 3 is an illustrative block diagram of a cartilage assessment server 300, which may be a server, a personal computer, a mainframe, a cluster of computing devices, a mobile device such as a smartphone, or some other suitable computing device. Referring to FIG. 1, assessment server 300 may correspond to assessment server 108. Assessment server 300 may evaluate the condition of cartilage associated with a joint, including its health and well-being, track a user's joint health, verify whether a user is authorized to view another user's information, or perform other suitable tasks. Assessment server 300 transmits and receives data through communications port 302. Communication processor 304 may send and receive information regarding joint noises, joint movement, and injury assessments through communication port 302. User database 306 stores information about users, which may include information identifying a device associated with a user; a user's age, weight, gender, physical activities, medical history, or other suitable information; who has permission to access a user's information or authorize a user to view another user's information; which users should be notified if a user is assessed as having a joint health problem; or other suitable information. Sound database 308 stores information regarding joint health determination, which may include movement patterns for a user to undertake during an assessment, sound patterns associated with cartilage health problems, sound patterns associated with healthy cartilage, or other suitable information. Cartilage health evaluation engine 310 may analyze sounds received from a user device 104 based on data in user database 306 and sound database 308 to calculate a user's cartilage health score.

The depicted communication port 302 is a network port which sends and receives assessment information via network 108. Assessment information may include baseline tasks, assessment tasks, user responses to tasks, performance thresholds, assessments of possible cartilage injury, reminders to take baseline tests, or other suitable information. Communication port 302 may include a 100BASE-TX port, a 1000BASE-T port, a 10 GBASE-T port, a WI-FI antenna, a BLUETOOTH antenna, a cellular antenna, or any other suitable network port. In certain implementations, there may be a different number of ports than are depicted. In certain implementations, communication port 302 may provide secure communications, such as by using the Secure Sockets Layer (SSL) protocol, the Transport Layer Security (TLS) protocol, or other suitable protocol.

Communication processor 304 may be a computer processor that sends and receives information via communications port 302. Communication processor 304 may transmit a reminder or instructions for performing a joint condition assessment task to a user device 104, may transmit information regarding a user's results to a user device 104, may transmit information regarding a user's cartilage condition assessment to one or more other designated users, or perform other suitable tasks. Such transmissions may be made in response to a request from a user device 104, or may be pushed to user device 104 under certain pre-determined conditions, such as a different user device 104 requesting that a user take a baseline test, the elapse of a predetermined amount of time, or some other suitable condition. As an illustrative example, if a user takes an assessment test and scores below a threshold, communications port 302 may push a warning regarding the user and a link to a server identifying nearby medical facilities to the user and other related users. Communication processor 304 may also revise information in user database 306 and sound database 308, such as by updating user's records in user database 306 based on information received from a user device 104 or recording sounds received from a user device 104 in sound database 308.

User database 306 may be a computer-readable and -writable medium storing information about a user, which may include one or more of the user's demographic information (e.g., age, gender, height, weight, activity levels, previous joint injury records), user devices 104 associated with the user, emergency contact information associated with the user, which other users are authorized to view the user's information, which receiving users should receive the user's information and under which circumstances, or other suitable information. As an illustrative example, a coach may designate when a game is taking place, and a referee may be designated as a recipient of a user's cartilage assessment results during the game period if the referee is within a predetermined distance from the user.

Sound database 308 may be a computer-readable and -writable medium storing information regarding sounds made by joints, which may include instructions to display to a user, sounds made by a user's joint, joint sounds exemplifying healthy or injured cartilage, rules for assessing joint sounds, or other suitable information. In some implementations, user database 306 may be partially or wholly combined with sound database 308.

Cartilage condition assessment engine 310 is a computer processor that may identify a joint health test to administer to a user, assess a user's cartilage health, identify other users to transmit user information to, or perform other suitable functions. As described in relation to FIG. 4, engine 310 may receive information from a user device 104 identifying a user and test conditions. Engine 310 may send instructions to a user via communication processor 304, in some implementations in response to a user request for test instructions. Engine 310 receives sounds made by a user's joint and recorded by user device 104, denoises the received sounds, and compares the denoised sounds to sounds in sound database 308 and information in user database 306 to calculate a health status of the cartilage associated with the joint. Engine 310 may provide the user with the health status, such as by transmitting a score between 1 and 100 to user device 104 via communication processor 304 for display; may forward the health status to a doctor or some other user identified by the user being evaluated; may recommend follow-up behavior to the user, such as identifying one or more local orthopedic doctors that the user might follow up with if the score is below a predetermined threshold; or perform some other suitable activity.

Cartilage condition assessment server 300 may evaluate cartilage health based on sounds made by an associated joint during motion, inform one or more users of the evaluation results, and recommend further actions for a user to take based on the evaluation results. Communication processor 304 may send and receive information regarding a user, joint tests, cartilage condition evaluations, and other suitable information via communications port 302, and store or retrieve such information from user database 306 and sound database 308 as appropriate. In some implementations, user database 306 and sound database 308 are preloaded with data from clinic studies. In some implementations, user database 306 and sound database 308 are supplemented as additional data is collected from additional subjects. Cartilage evaluation engine 310 analyzes sounds produced by a joint in light of the characteristics of the user, and generates a cartilage health score accordingly.

In some implementations, cartilage assessment server 300 may be combined, in whole or in part, with user device 200. As an illustrative example, cartilage evaluation engine 310 may be implemented on a user device 200, which may retrieve information from user database 306 or sound database 308 to locally calculate a user's cartilage health score. It will be appreciated that as user database 306 and sound database 308 grow to include additional data, the systems according to the present disclosure achieve increased accuracy and can ascribe statistical significance to more subtle trends and tendencies. In some implementations, the availability of additional data points allows a closer correlation to be determined. In some implementations, the availability of additional data points allows further training of a neural network or other learning system.

Figure 4:
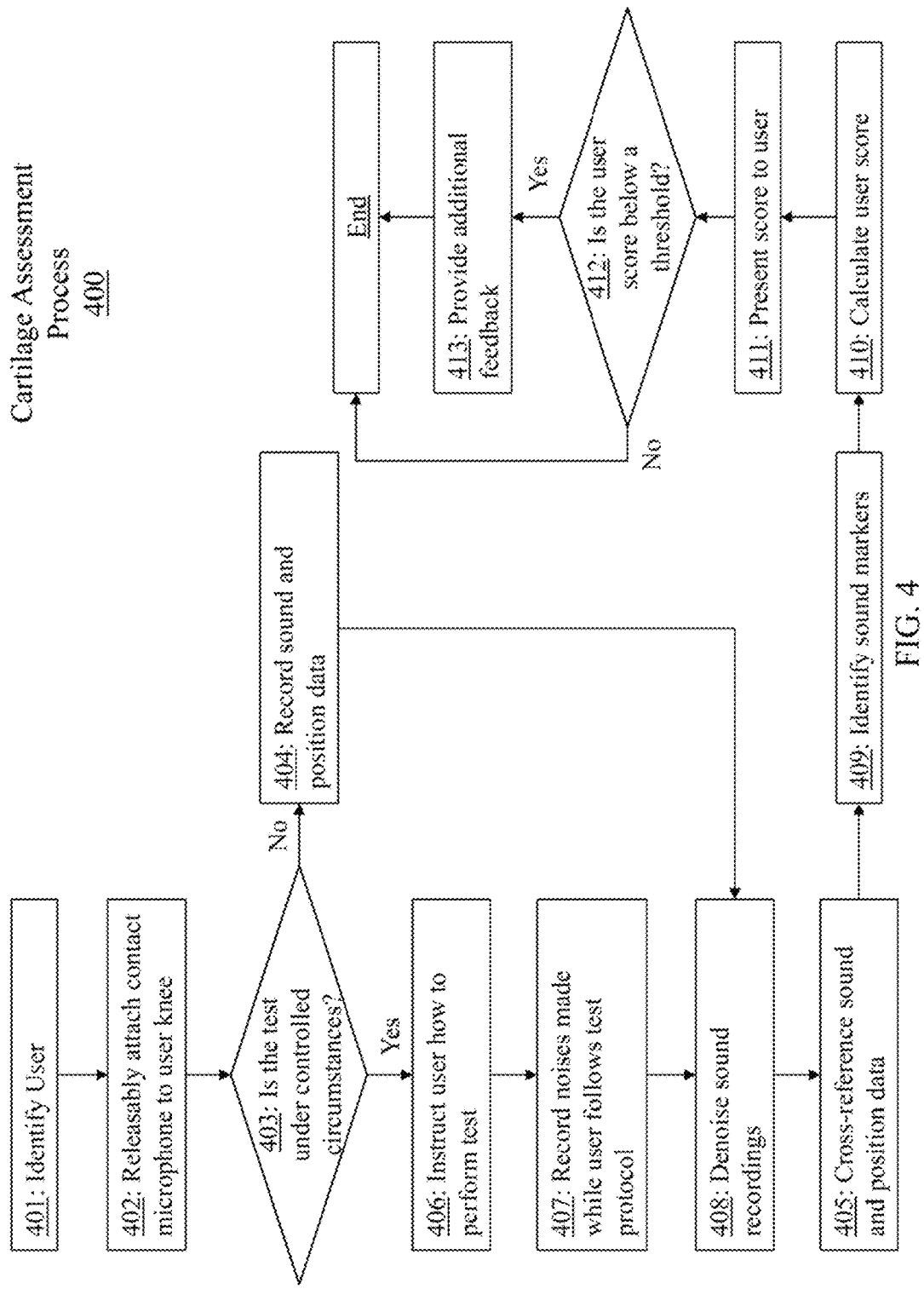
FIG. 4 is a flow chart of a cartilage assessment process, according to various embodiments of the present disclosure.

FIG. 4 is an illustrative flow chart of a cartilage condition assessment process 400. Cartilage condition assessment process 400 assesses a user's cartilage condition and informs the user of the result; as depicted, process 400 is directed towards assessing knee health, but it will be appreciated that process 400 may also or alternatively apply to other joints. Referring to FIGS. 2 and 3, process 400 begins with step 401, in which communication processor 304 identifies a user being assessed based on information received from user device 200. Communication processor 304 may identify the user based on whether the user is associated with the user device 200, based on a user's input, or based on some other suitable information. In step 402, a contact microphone is releasably attached to a user's knee, which may include securing the microphone in place with an adhesive, with a resilient band, or with some other suitable implement.

In step 403, evaluation engine 310 identifies the variety of test being performed. A user's knee sounds may be recorded under controlled conditions (e.g., while the user sits on an examination table and flexes the user's knee, such as for calibration or assessing a baseline condition of the cartilage) or may be recorded under more realistic use (e.g., while walking or running). A user may signal evaluation engine 310 regarding a test variety using a user device 104 or some other suitable device (e.g., by using a selector switch on a user device 104, by making a selection on a website, or by sending a text message to a server). In some implementations, a user device 104 automatically generates a signal indicating a test variety based on the status of the device itself (e.g., based on whether the device is located in a designated region, whether the device is connected to a designated network, or whether the device is contacting a joint). In some implementations, evaluation engine 310 may also identify which joint is being evaluated during step 403, and evaluate recorded sounds accordingly.

If step 403 indicates that the evaluation will not be performed under controlled conditions, process 400 proceeds to step 406; otherwise process 400 proceeds to step 404. In step 404, user device 200 generates and transmits sound and position data to server 300 while the user acts normally. In some implementations, user device 200 may record such data on a local buffer for later transmission, and may transmit buffered data based on conditions such as the availability of a network connection, the amount of space left in the buffer, or other suitable conditions. In some implementations, user device 200 maintains a local database containing data and performs synchronization with server 300. After step 404, process 400 proceeds to step 408, described below.

If step 403 indicates that the test will be controlled under controlled conditions, process 400 proceeds with step 406, in which evaluation engine 310 generates instructions regarding how to perform the test. The instructions may be provided to the user via output 208 or through some other suitable channel, and may indicate a starting position the user should assume, leg movements to make during the test, a signal the user should send to evaluation engine 310 when beginning the test, or other suitable information. As an illustrative example, step 406 may instruct a user to sit down with her legs hanging freely and flex her knee between 0° and 90° a number of times (e.g., five times), allowing microphone 204 to pick up knee sounds without having the ankle, hip, or meniscus generate any confounding noise. In step 407, microphone 204 records sounds made by the knee while the user moves his or her leg in accordance with the test protocol. In some implementations, position sensor 206 may also record knee movements during step 407. Communication processor 210 may forward the recorded sounds to server 300 for processing.

In step 408, evaluation engine 310 denoises the received sounds, whether they were recorded during real-life activity in step 404 or during an established protocol during step 407. Evaluation engine 310 may denoise received sounds by averaging several sounds taken during equivalent periods (e.g., during cycles of an established protocol, or during movements that position sensor 206 indicate to be similar), by identifying noise picked up by secondary microphones as associated with other joints and correcting recorded sounds accordingly, or by other suitable measures. In general, denoising comprises removing noise or unnecessary components of the received sounds. It will be appreciated that various denoising techniques known in the art are suitable for use according the present disclosure. In step 405, evaluation engine 310 cross-references the sound and position data received from user device 200 to identify correlations between knee movements and sounds. In some implementations, user device 200 may perform step 405 before transmitting the cross-referenced data to server 300.

In step 409, evaluation engine 310 identifies markers in the denoised sound, which may include one or more of the frequency of sounds, the duration of sounds, the wavelengths present in sounds, the correlation between sounds and position or movement of the knee, the power spectral density function of sounds, or some other suitable markers. In step 410, evaluation engine 310 calculates a user score by comparing the identified markers to sounds in sound database 308 and information in user database 306, which may include comparing the markers to knee sounds produced by similar users, comparing the markers to the general population of knee sounds and then correcting the score based on user information, or some other suitable combination of sound and user data. Evaluation engine 310 may calculate the user score based on a neural network using demographic information and sound markers as inputs and a health score as an output, where the neural network is trained using markers of prerecorded sounds associated with both healthy and unhealthy knees; by identifying one or more prerecorded sounds that have markers most similar to the markers identified in step 409, averaging health scores associated with the prerecorded sounds, and normalizing using user information stored in user database 306; by comparing the identified markers to markers for other users with similar demographics and determining which percentile the user falls into; or based on some other suitable measure. In some implementations, evaluation engine 310 may identify a health status of a knee by performing wavelet analysis of the sound using wavelets based on previously identified unhealthy knee sounds.

In step 411, output 208 presents the score (e.g., a number between 1 and 100, a number between 1 and 10, or a description of the knee as "healthy" or "needs further testing") to the user. In step 412, evaluation engine 310 determines if the score is below a predefined threshold. If the score is above the threshold, then the knee is considered healthy, and process 400 ends. If not, process 400 ends with step 413, in which evaluation engine 310 provides additional feedback. In some implementations, additional feedback includes identifying nearby medical service providers to the user. In some implementations, evaluation engine 310 may also or alternatively suggest ameliorative measures the user may take, such as ceasing strenuous activity or varying stride, gait, or other relevant motions. In some implementations, the users are provided with educational materials regarding better practices for joint maintenance.

In some implementations, process 400 may also output a warning to other, designated receiving users, e.g., a coach or a medical professional.

Figure 5:
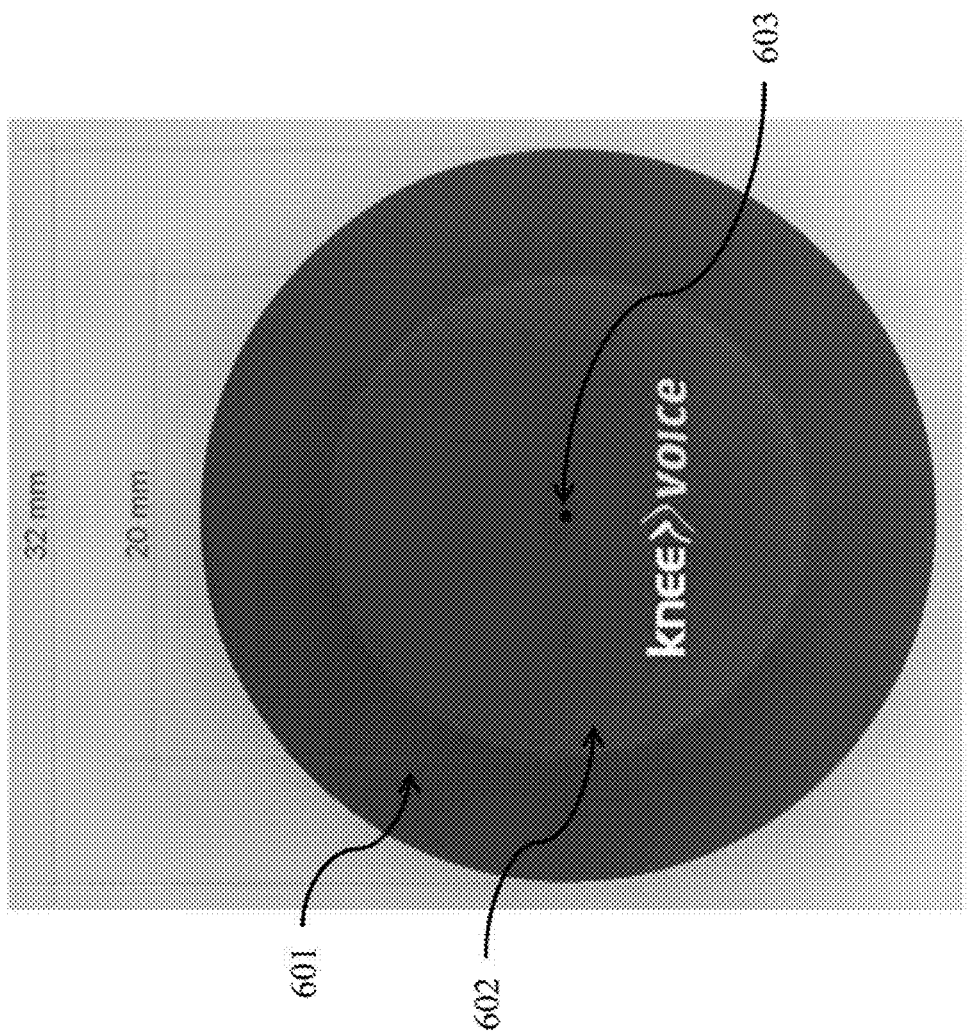
FIG. 5 is a plan view of a device for measuring joint condition according to various embodiments of the present disclosure.

FIG. 5 is a plan view of a an exemplary housing 500 for a joint condition sensor according to various embodiments of the present disclosure. Housing 500 includes a substantially circular flange 601 with a centrally located substantially circular elevated central region 602. In some embodiments, central region 602 accommodates on board electronics and an integrated microphone or accelerometer as set forth above with regard to FIG. 2. In some embodiments, a vent hole 603 is included to allow pressure equalization between the interior and exterior of housing 500. In some embodiments, flange 601 has a diameter of about 32 mm, while central region 602 has a diameter of about 20 mm. In various embodiments, housing 500 comprises a polymer such as silicone, polyethylene, polyvinyl chloride, polyurethane, or polylactide.

Figure 6:
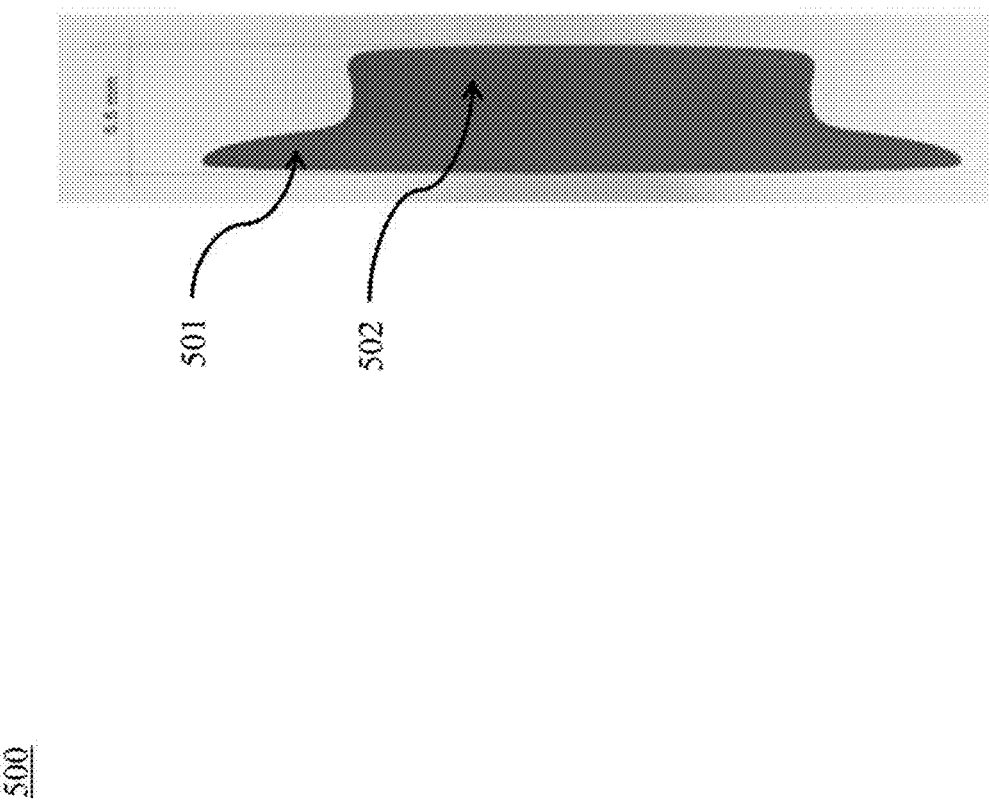
FIG. 6 is a side view of a device for measuring joint condition according to various embodiments of the present disclosure.

FIG. 6 is a side view of housing 500.

Figure 7:
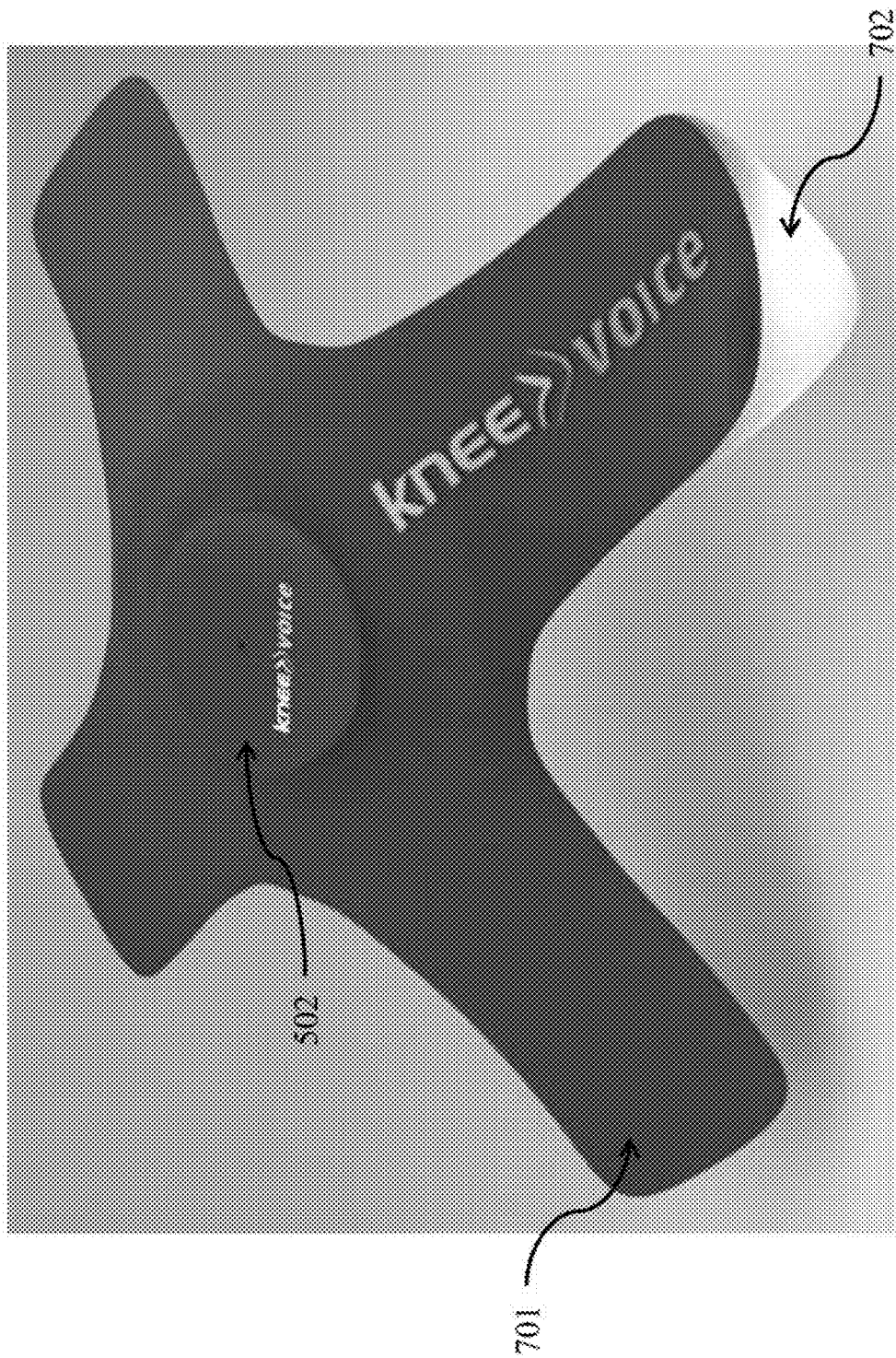
FIG. 7 is a perspective view of a device for measuring joint condition according to various embodiments of the present disclosure.

FIG. 7 is a perspective view of housing 500 assembled with an exemplary adhesive patch 701. In this exemplary embodiments, central region 502 of housing 500 extends through a substantially circular opening in patch 701. Flange 501 thereby ensures that housing 500 remains fixed relative to patch 701 when patch 701 is applied to a joint. In some embodiments, patch 701 is substantially cruciform, having substantially perpendicular legs crossing in a central region. This configuration enables patch 701 to conform to various sizes and curvatures of joint. In some embodiments, patch 701 is backed with an adhesive suitable for use on a human subject. In some such embodiments, a paper or plastic backing layer 702 is included to protect the adhesive prior to application.

Figure 8:
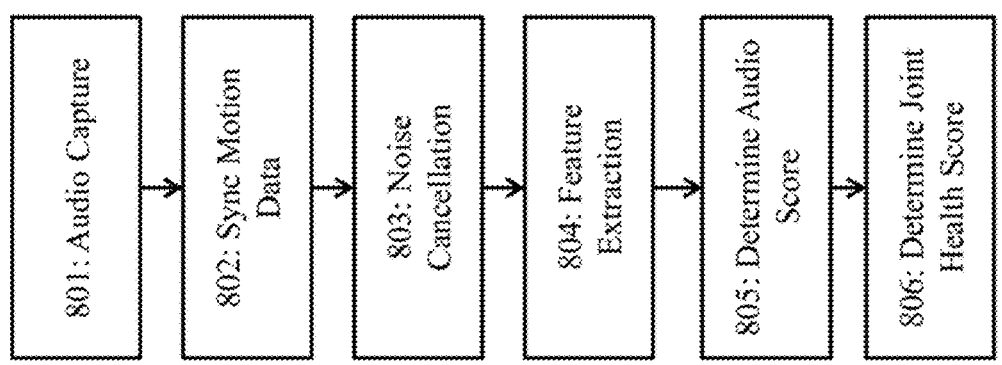
FIG. 8 is a flow chart of a method for determining a joint health score according to various embodiments of the present disclosure.

FIG. 8 illustrates a method of determining a joint score according to various embodiments of the present disclosure. As generally outlined above, at step 801, raw audio is captured of the knee or other joint. In some embodiments, a device such as that described with reference to FIGS. 5-7 is used to capture the audio using a series of sensors and microphones (e.g., accelerometers and contact microphones). In some embodiments, at 802, motion data (e.g., from an accelerometer) or other sensor data is synchronized with the audio. In some embodiments, such motion data is used to assist in noise cancellation, for example by providing periodicity information on subject motion. In some embodiments, such motion data is used to locate where a joint noise is coming from. For example, by providing motion data to the learning system described below, it may be trained to differentiate between sounds within different regions of a joint. In some embodiments, at 803, noise cancellation is applied to the raw audio to isolate the noise that is generated by the knee or other joint. Such noise may include ambient noise, noise generated by other body parts, or electrostatic noise created by data transmission. In various embodiments, noise cancellation comprises active or passive noise cancellation. In various embodiments using active noise cancellation, an outward facing microphone is used to collect environmental noise for removal from the joint audio signal. In various embodiments, a bandpass filter is applied to remove noise not associated with the joint. In various embodiments, the housing such as that described above with regard to FIGS. 5-7 includes a contact microphone and the casing material is absorptive of external noise, providing passive noise cancellation. It will be appreciated that a variety of active and passive noise cancellation techniques are suitable for use according to the present disclosure. For example, an integrated DSP may provide standard noise cancellation techniques in line with the audio source. In another example, a fast Fourier transform (FFT) is applied to the signal to identify and remove periodic noise. In another example, multiple microphones are used in combination with an FFT to pinpoint the origin of noise.

At 804, the audio is processed to extract a plurality of features. In some embodiments, the features include one or more of: signal frequency, amplitude, zero-crossing rate, entropy of energy, spectral centroid, spectral spread, mel-frequency cepstral coefficients (MFCCs), and chroma vector. Each feature is described further below with reference to FIGS. 9-12. At 805, the feature vector is provided to a trained classifier to determine an audio score. In some embodiments, the trained classifier is a random decision forest. However, it will be appreciated that a variety of other classifiers are suitable for use according to the present disclosure, including linear classifiers, support vector machines (SVM), or neural networks such as recurrent neural networks (RNN). In some embodiments, the audio score may range from 0-100.

In various exemplary embodiments, the classifier is trained by providing a plurality of audio recordings to a physician, who determine a score. For example, an orthopedist may be provided a recording having a given feature vector. After listening to the recording, the doctor assigns a target score or score range. In this way, the classifier learns to associate a given score with given audio features. In some embodiments, the doctor is provided with a group of samples that is representative of a single quartile, and is asked to confirm a score generated by the classifier. It will be appreciated that various training algorithms known in the art are suitable for use according to the present disclosure based on the type of classifier applied. After manual classification and training of the classifier, the classifier is applied to determine audio scores for newly collected audio.

At 806, a joint health score is determined from the audio score and additional subject-specific parameters. In some embodiments, the additional subject-specific parameters include one or more of pain, BMI, age, gender, surgical interventions or treatments, and exercise frequency. In some embodiments, the joint health score ranges form 0-100, with 0 corresponding to very damaged cartilage and 100 corresponding to perfect cartilage.

In some embodiments, a value Y is computed relating subjective pain to the audio score according to Equation 1, where A is the previously computed audio score and P is a user-reported pain factor. In some embodiments, P is given on a 0-100 scale such as the Numeric Rating Scale (NRS-11). Y thus provides user-specific context for the audio score. According to various embodiments, an average value of Y for all users having a given attribute is computed for normalization purposes. Thus, in the below, an average value for Y over all users having a BMI in a given range is used. In this way, variations in reported pain value can be corrected when computing the final joint health score. In some embodiments, Y is an average over multiple samples, while in some embodiments Y is limited to a single sample.

$$Y = A*P \qquad \text{Equation 1}$$

In some embodiments, the joint health score is given by Equation 2, where Y is defined above. Y(X) is a function providing the average value of Y among subjects having the argument attribute X or having attribute X within a predetermined range. W(X) is a function providing the weight to apply to the argument attribute. B is BMI, A is age, G is gender, M is medical condition, and P is a frequency of physical activity. Accordingly, Y(B) is the average Y score for all patients having a BMI within the same range as the current patient; Y(A) is the average Y score for all patients having an age within the same range as the current patient. Y(G) is the average Y score for all patients having the same gender as the current patient; Y(M) is the average Y score for all patients having the same or similar medical conditions of the current patient; Y(P) is the average Y score for all patients having frequency of physical activity within the same range as the current patient. The weights W vary from attribute to attribute and allows each attribute to have a variable impact on the overall score. It will be appreciated that although the present example focuses on five particular attributes, additional patient attributes may be included in various embodiments according to the present disclosure.

$$W(B)\frac{Y}{Y(B)} + W(A)\frac{Y}{Y(A)} + W(G)\frac{Y}{Y(G)} + W(M)\frac{Y}{Y(M)} + W(P)\frac{Y}{Y(P)} \qquad \text{Equation 2}$$

Figure 9:
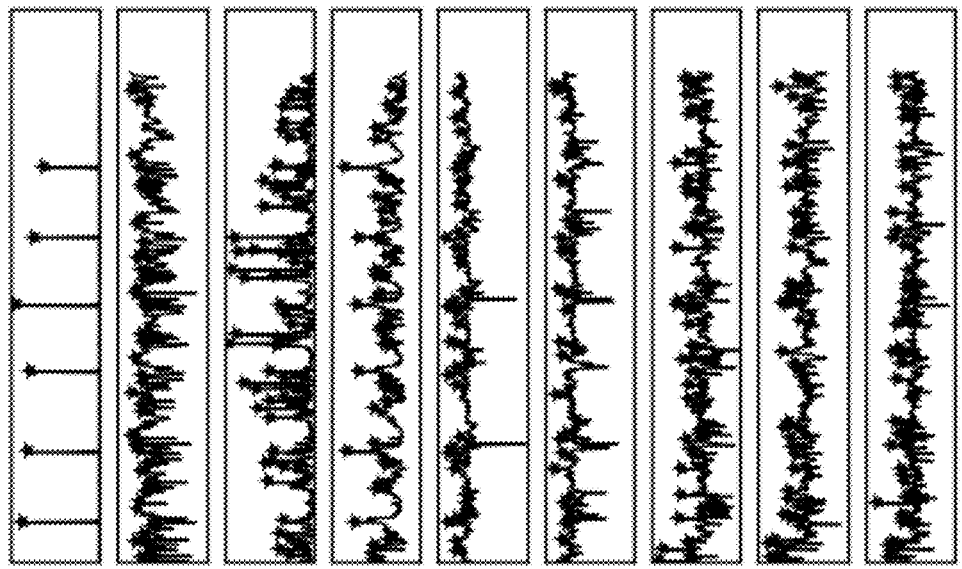
FIG. 9 is an exemplary beat extraction for exemplary joint audio according to various embodiments of the present disclosure.
Figure 9:
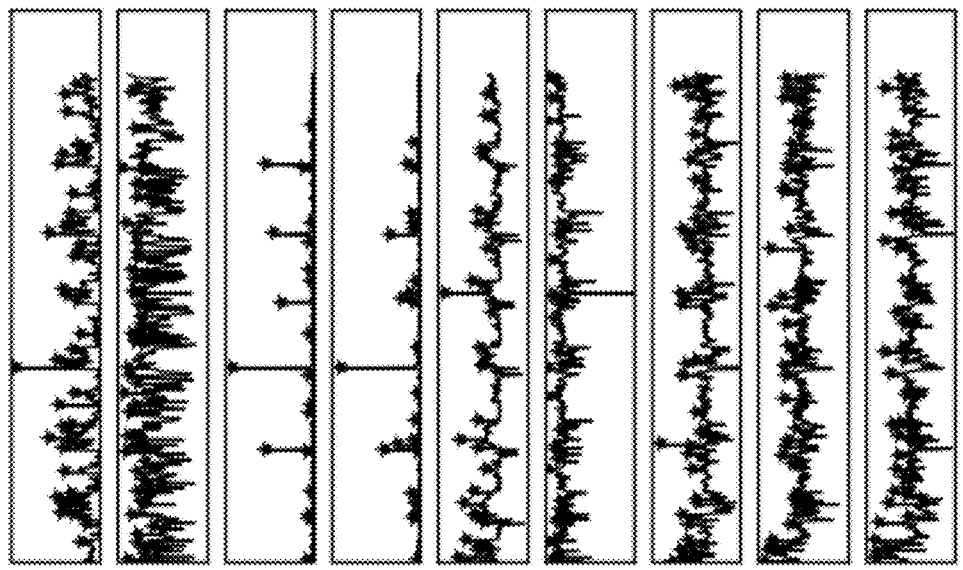

Referring to FIG. 9, exemplary beat extraction is illustrated for exemplary joint audio. In various embodiments, beat extraction is used to generated a feature vector. As set forth herein, such vectors may be compared with other beat vectors to detect variations from the mean. Similarly, such beat vectors may be supplied to a learning system as a component of joint health detection.

Figure 10:
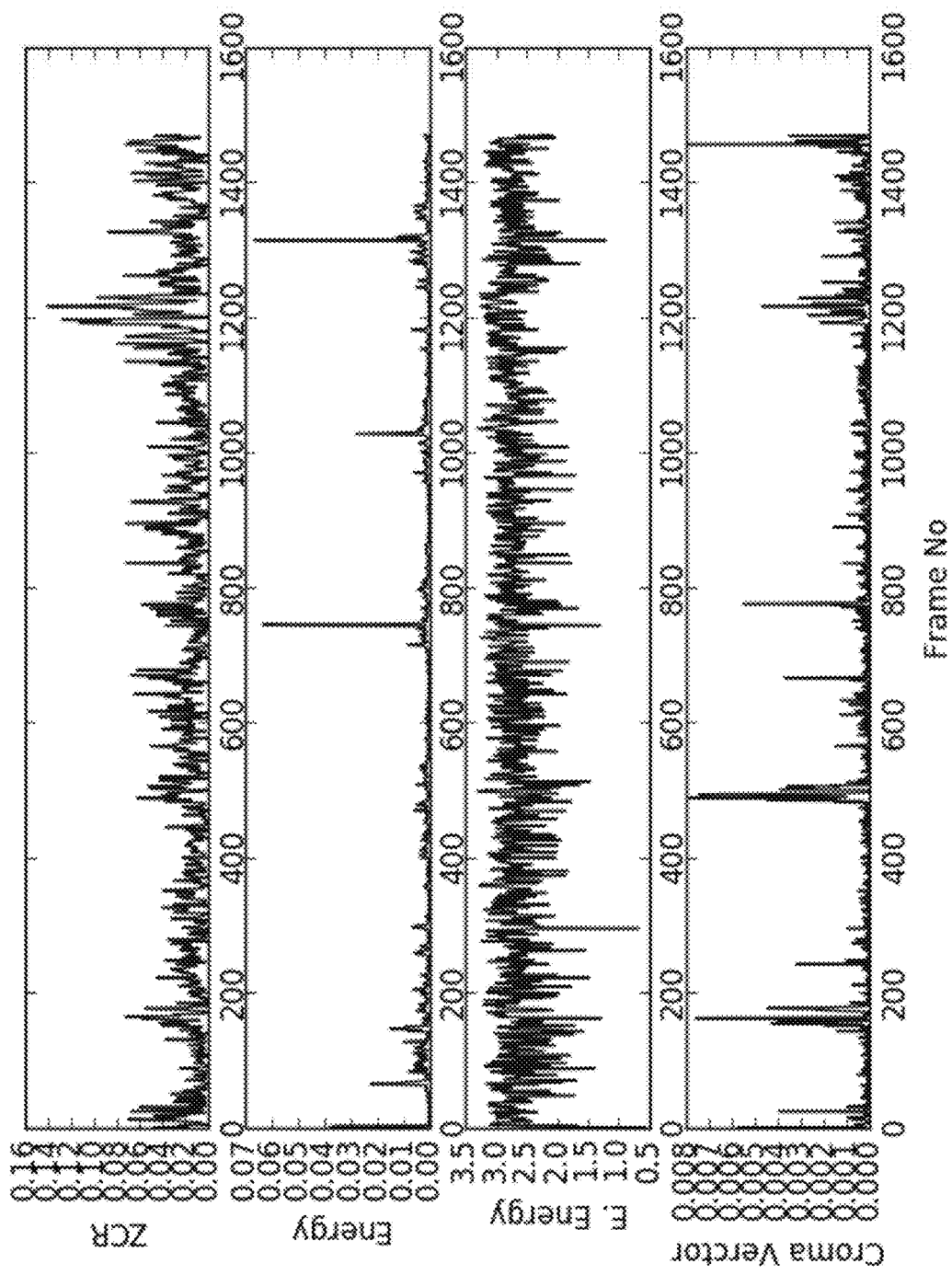
FIG. 10 is a series of graphs of the zero crossing rate (ZCR), energy, entropy of energy, and chroma vector for exemplary joint audio according to various embodiments of the present disclosure.

Referring to FIG. 10, the zero crossing rate (ZCR), energy, entropy of energy, and chroma vector are illustrated for exemplary joint audio. The zero crossing rate corresponds to the rate of sign-changes of the signal during the duration of a particular frame. The energy is the sum of squares of the signal values, normalized by the respective frame length. The entropy of energy corresponds to the sub-frames' normalized energies. It can be interpreted as a measure of abrupt changes.

Figure 11:
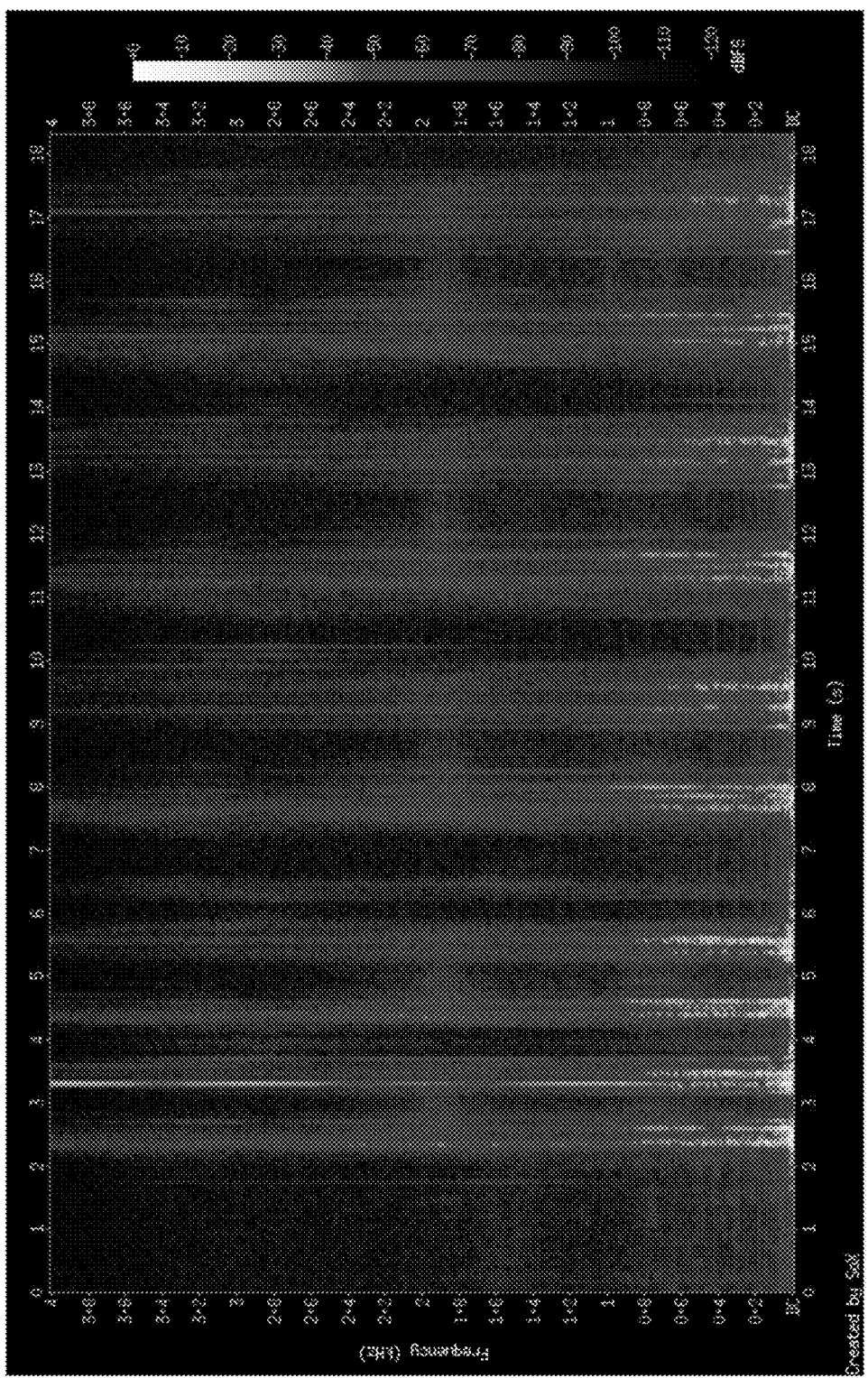
FIG. 11 is a spectrogram illustrating the frequency over time of exemplary joint audio according to various embodiments of the present disclosure.

Referring to FIG. 11, a spectrogram is provided, illustrating the frequency over time of exemplary joint audio is depicted. From this, the spectral centroid, spectral spread, spectral entropy, spectral flux, and spectral rolloff may be computed. The spectral centroid corresponds to the center of gravity of the spectrum. The spectral spread corresponds to the second central moment of the spectrum. The spectral entropy corresponds to the entropy of the normalized spectral energies for a set of sub-frames. The spectral flux corresponds to the squared difference between the normalized magnitudes of the spectra of two successive frames. Spectral rolloff corresponds to the frequency below which 90% of the magnitude distribution of the spectrum is concentrated.

Figure 12:
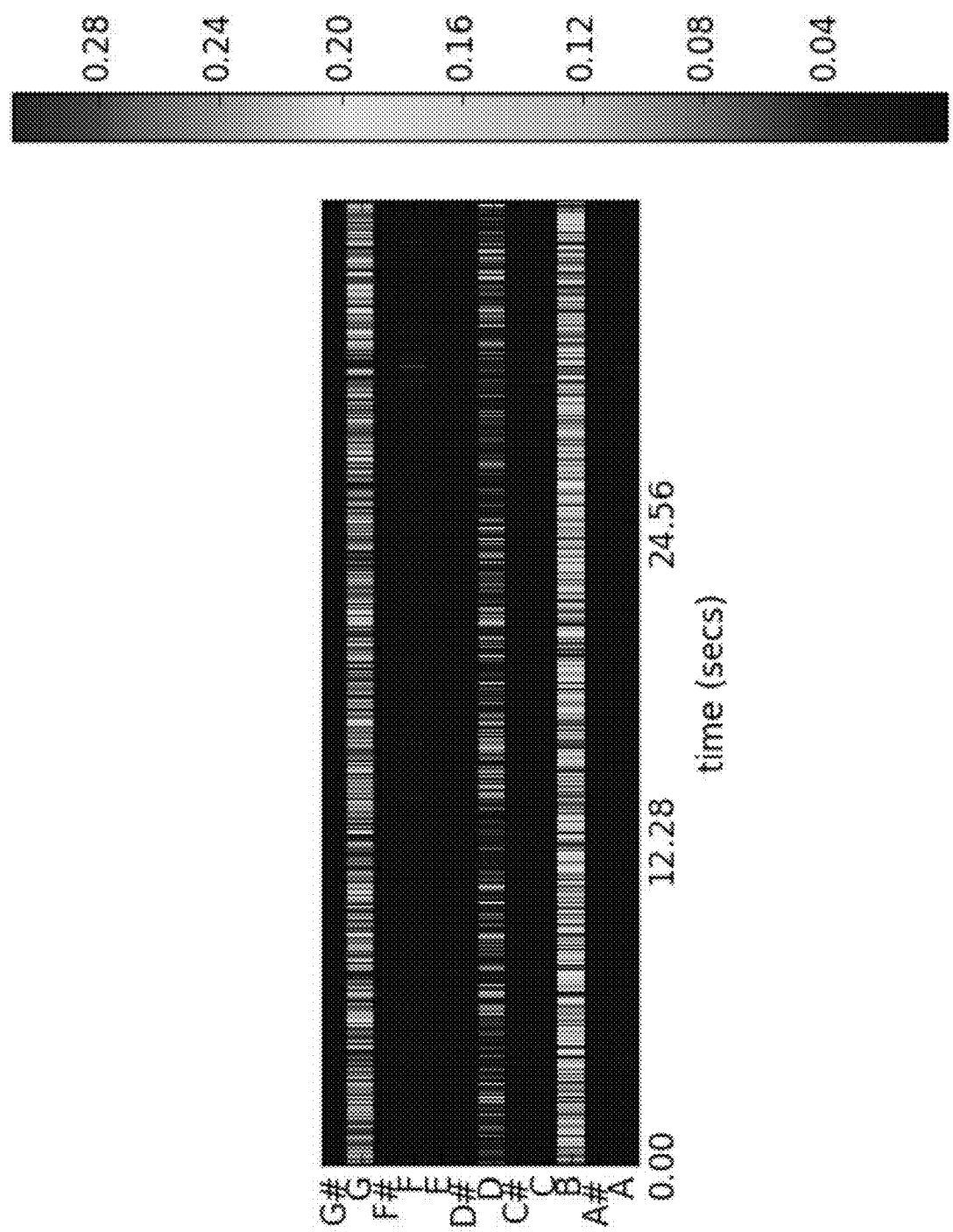
FIG. 12 is a chromagram illustrating the chroma features of exemplary joint audio according to various embodiments of the present disclosure.

Referring to FIG. 12, a chromagram is provided, illustrating the chroma features of exemplary joint audio is depicted. From this, the chroma vector and chroma deviation may be computed. The chroma vector provides a 12-element representation of spectral energy, where the bins represent the 12 equal-tempered pitch classes of western-type music (semitone spacing). Chroma deviation provides the standard deviation of the 12 chroma coefficients.

Figure 13:
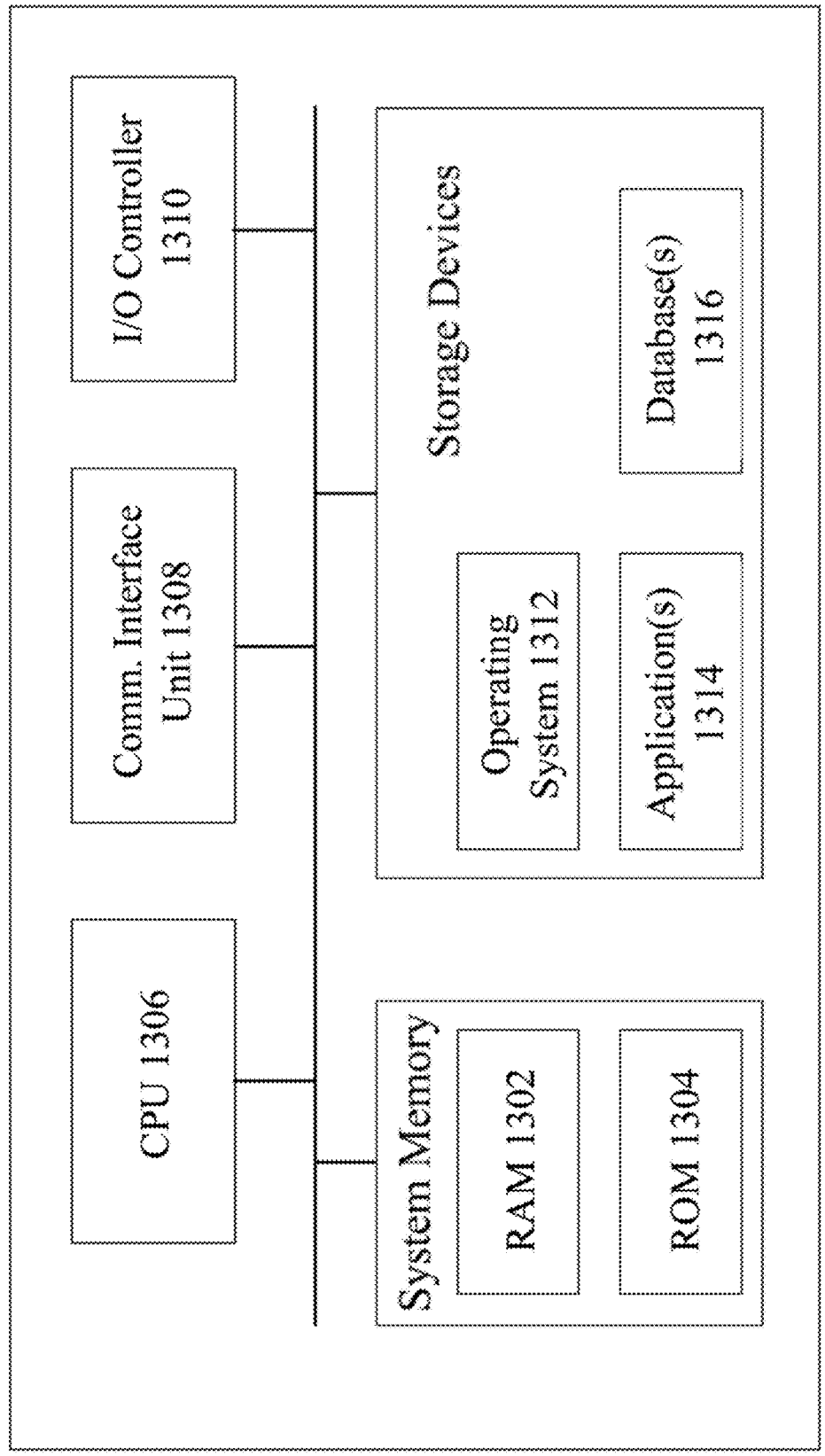
FIG. 13 is a block diagram of a computing device for performing any of the processes described herein, according to an illustrative implementation.

FIG. 13 is a block diagram of a computing device that can be used to implement or support any of the components of the system of FIG. 1, 2, or 3, and for performing, any of the processes described herein. Cartilage condition assessment server 300 may be implemented on one or more computing devices 1300 having suitable circuitry, and user device 104 may communicate with assessment server 108 through one or more computing devices 1300 having suitable circuitry. In certain aspects, a plurality of the components of cartilage condition assessment system 100 may be included within one computing device 1300. In certain implementations, a component of cartilage condition assessment system 100 may be implemented across several computing devices 1300.

The computing device 1300 comprises at least one communications interface unit, an input/output controller 1310, system memory, and one or more data storage devices. This can support a network connection, such as a connection to network 106 in FIG. 2. The system memory includes at least one random access memory (RAM 1302) and at least one read-only memory (ROM 1304). RAM 1302 can support the user database 1310 of FIG. 2, for example. All of these elements are in communication with a central processing unit (CPU 1306) to facilitate the operation of the computing device 1300. The computing device 1300 may be configured in many different ways. For example, the computing device 1300 may be a conventional standalone computer or, alternatively, the functions of computing device 1300 may be distributed across multiple computer systems and architectures. In FIG. 13, the computing device 1300 may be linked, via network or local network, to other servers or systems.

The computing device 1300 may be configured in a distributed architecture, wherein databases and processors are housed in separate units or locations. Some units perform primary processing functions and contain, at a minimum, a general controller or a processor and a system memory. In distributed architecture implementations, each of these units may be attached via the communications interface unit 508 to a communications hub or port (not shown) that serves as a primary communication link with other servers, client or user computers, and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM, and TCP/IP.

The CPU 1306 comprises a processor, such as one or more conventional microprocessors and one or more supplementary co-processors such as math co-processors for offloading workload from the CPU 1306. The CPU 1306 is in communication with the communications interface unit 1308 and the input/output controller 1310, through which the CPU 1306 communicates with other devices such as other servers, user terminals, or devices. The communications interface unit 1308 and the input/output controller 1310 may include multiple communication channels for simultaneous communication with, for example, other processors, servers, or client terminals.

The CPU 1306 is also in communication with the data storage device. The data storage device may comprise an appropriate combination of magnetic, optical, or semiconductor memory, and may include, for example, RAM 1302, ROM 1304, flash drive, an optical disc such as a compact disc, or a hard disk or drive. The CPU 1306 and the data storage device each may be, for example, located entirely within a single computer or other computing device; or connected to each other by a communication medium, such as a USB port, serial port cable, a coaxial cable, an Ethernet cable, a telephone line, a radio frequency transceiver, or other similar wireless or wired medium or combination of the foregoing. For example, the CPU 1306 may be connected to the data storage device via the communications interface unit 1308. The CPU 1306 may be configured to perform one or more particular processing functions.

The data storage device may store, for example, (i) an operating system 1312 for the computing device 1300; (ii) one or more applications 1314 (e.g., computer program code or a computer program product) adapted to direct the CPU 1306 in accordance with the systems and methods described here, and particularly in accordance with the processes described in detail with regard to the CPU 1306; or (iii) database(s) 1316 adapted to store information that may be utilized to store information required by the program. The depicted database 1316 can be any suitable database system, and can be a local or distributed database system.

The operating system 1312 and applications 1314 may be stored, for example, in a compressed, an uncompiled and an encrypted format, and may include computer program code. The instructions of the program may be read into a main memory of the processor from a computer-readable medium other than the data storage device, such as from the ROM 1304 or from the RAM 1302, or from a computer data signal embodied in a carrier wave, such as that found within the well-known Web pages transferred among devices connected to the Internet. While execution of sequences of instructions in the program causes the CPU 1306 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions in relation to an assessment system as described herein. The program also may include program elements such as an operating system 1312, a database management system, and "device drivers" that allow the processor to interface with computer peripheral devices (e.g., a video display, a keyboard, a computer mouse, etc.) via the input/output controller 1310.

The term "computer-readable medium" as used herein refers to any non-transitory medium that provides or participates in providing instructions to the processor of the computing device 1300 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, an SSD, a RAM, a PROM, an EPROM or EEPROM (electronically erasable programmable read-only memory), a FLASH-EEPROM, any other memory chip or cartridge, or any other non-transitory medium from which a computer can read. In various embodiments, one or more of said computer readable media are accessible via a network, such as in a NAS or SAN arrangement.

Various forms of computer readable media may be involved in carrying one or more sequences of one or more instructions to the CPU 1306 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 1300 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic, or optical signals, which are exemplary forms of wireless communications or data streams that carry various types of information.

Some implementations of the above described may be implemented by the preparation of application-specific integrated circuits or by interconnecting an appropriate network of conventional component circuits, as will be apparent to those skilled in the art. Those of skill in the art would understand that information and signals may be represented using any of a variety of different technologies and techniques. For example, data, instructions, requests, information, signals, bits, symbols, and chips that may be referenced throughout the above description may be represented by voltages, currents, electromagnetic waves, magnetic fields or particles, optical fields or particles, or any combination thereof.

While various embodiments of the present disclosure have been shown and described herein, it will be obvious to those skilled in the art that such embodiments are provided by way of example only. Numerous variations, changes, and substitutions will now occur to those skilled in the art without departing from the disclosure. For example, assessment system 100 may be implemented entirely on a user device 104, which may eliminate the need for an assessment server 108; a user device 200 may offer an option to contact a medical professional n response to a poor assessment test or evaluation; a user device 200 may generate comparisons between a user's most recent evaluation and previous evaluations to generate an alert if the comparison suggests a pattern of decline; cartilage health scores may be based in part on similar evaluations of populations similar to the user, standardized thresholds, or clinically calibrated thresholds associated with injury risk; sounds recorded from users may be standardized at a population level, and used to document the benefits of pharmacological or surgical therapeutic interventions (e.g., the use of chondral protectors, intra-articular visco-supplements, or arthroscopy). It should be understood that various alternatives to the embodiments of the disclosure described herein may be employed in practicing the disclosure. Elements of an implementation of the systems and methods described herein may be independently implemented or combined with other implementations. It is intended that the following claims define the scope of the disclosure and that methods and structures within the scope of these claims and their equivalents be covered thereby.

What is claimed is:

1. A system comprising:
   a contact microphone;
   a processor operatively connected to the contact microphone;
   a computer readable storage medium having program instructions embodied therewith, the program instructions configured to cause the processor to perform a method comprising:
     receiving from the contact microphone audio comprising sounds emanating from a human patellofemoral joint of a subject during knee flexion;
     extracting a plurality of features from the audio by the processor;
     providing the plurality of features to a trained classifier;
     obtaining from the trained classifier a first numeric score indicative of patellofemoral joint health;
     obtaining a pain value reported by the subject or a characteristic of the subject;
     computing a second score indicative of joint health from the first score, wherein computing the second score comprises weighting the first score according to the pain value reported by the subject or according to the characteristic of the subject, wherein said weighting comprises applying a mathematical function to the first score; and
     displaying the second score with an indication to perform follow-up when the second score is below a predetermined threshold.

2. The system of claim 1, the method further comprising:
   capturing the audio via the contact microphone in contact with the exterior of a human knee.

3. The system of claim 2, wherein the contact microphone is in contact with an anterior patellar surface.

4. The system of claim 1, the method further comprising:
   canceling noise from the audio prior to extracting the plurality of features.

5. The system of claim 4, wherein canceling noise comprises:
   capturing an ambient audio signal by an outward facing microphone;
   removing the ambient audio signal from the audio.

6. The system of claim 4, wherein canceling the noise comprises:
   applying a bandpass filter to the audio.

7. The system of claim 1, wherein the plurality of features comprises zero-crossing rate, entropy of energy, spectral centroid, spectral spread, mel-frequency cepstral coefficients, or chroma vector.

8. The system of claim 1, wherein the trained classifier comprises a random decision forest.

9. The system of claim 1, wherein the trained classifier comprises a neural network.

10. The system of claim 1, wherein the trained classifier comprises a support vector machine.

11. The system of claim 1, wherein the characteristic comprises body mass index, age, gender, existing medical condition, or frequency of physical activity.

12. The system of claim 1, the method further comprising outputting the first score or the second score to a user.

13. A method comprising:
    receiving from a contact microphone audio comprising sounds emanating from a human patellofemoral joint of a subject during knee flexion;
    extracting a plurality of features from the audio by a processor;
    providing the plurality of features to a trained classifier;
    obtaining from the trained classifier a first numeric score indicative of patellofemoral joint health;
    obtaining a pain value reported by the subject or a characteristic of the subject;
    computing a second score indicative of joint health from the first score, wherein computing the second score comprises weighting the first score according to the pain value reported by the subject or according to the characteristic of the subject, wherein said weighting comprises applying a mathematical function to the first score; and
    displaying the second score with an indication to perform follow-up when the second score is below a predetermined threshold.

14. The method of claim 13, further comprising:
    capturing the audio via a contact microphone in contact with the exterior of a human knee.

15. The method of claim 14, wherein the contact microphone is in contact with an anterior patellar surface.

16. The method of claim 13, further comprising:
    canceling noise from the audio prior to extracting the plurality of features.

17. The method of claim 15, wherein canceling noise comprises:
    capturing an ambient audio signal by an outward facing microphone;
    removing the ambient audio signal from the audio.

18. The method of claim 15, wherein canceling the noise comprises:
    applying a bandpass filter to the audio.

19. The method of claim 13, wherein the plurality of features comprises zero-crossing rate, entropy of energy, spectral centroid, spectral spread, mel-frequency cepstral coefficients, or chroma vector.

20. The method of claim 13, wherein the trained classifier comprises a random decision forest.

21. The method of claim 13, wherein the trained classifier comprises a neural network.

22. The method of claim 13, wherein the trained classifier comprises a support vector machine.

23. The method of claim 13, wherein the characteristic comprises body mass index, age, gender, existing medical condition, or frequency of physical activity.

24. The method of claim 13, further comprising outputting the first score or the second score to a user.

* * * * *